United States Patent
Murata et al.

(10) Patent No.: US 11,484,258 B2
(45) Date of Patent: Nov. 1, 2022

(54) FREE RADICAL CONSUMPTION SPEED INFORMATION ACQUISITION METHOD AND NASH DETERMINATION METHOD

(71) Applicant: KYUSHU UNIVERSITY, NATIONAL UNIVERSITY CORPORATION, Fukuoka (JP)

(72) Inventors: Masaharu Murata, Fukuoka (JP); Fuminori Hyodo, Fukuoka (JP); Makoto Hashizume, Fukuoka (JP); Ryosuke Nakata, Fukuoka (JP); Tomohiko Akahoshi, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 944 days.

(21) Appl. No.: 16/309,730

(22) PCT Filed: Jun. 9, 2017

(86) PCT No.: PCT/JP2017/021524
§ 371 (c)(1),
(2) Date: Dec. 13, 2018

(87) PCT Pub. No.: WO2017/217340
PCT Pub. Date: Dec. 21, 2017

(65) Prior Publication Data
US 2019/0133517 A1 May 9, 2019

(30) Foreign Application Priority Data
Jun. 13, 2016 (JP) .............................. JP2016-117335

(51) Int. Cl.
*A61B 5/055* (2006.01)
*G01N 24/12* (2006.01)
(Continued)

(52) U.S. Cl.
CPC ............ *A61B 5/4839* (2013.01); *A61B 5/055* (2013.01); *A61B 5/4244* (2013.01);
(Continued)

(58) Field of Classification Search
CPC ..... A61B 5/4839; A61B 5/055; A61B 5/4244; A61B 5/4848; A61B 2503/40;
(Continued)

(56) References Cited

U.S. PATENT DOCUMENTS

2008/0311593 A1* 12/2008 Younossi ............... G01N 33/68
435/14
2009/0028798 A1* 1/2009 Mitchell ............... A61K 49/10
424/9.33
(Continued)

FOREIGN PATENT DOCUMENTS

JP 5252444 B2 7/2013
JP 2015148555 A * 8/2015
(Continued)

OTHER PUBLICATIONS

Office Action issued in the counterpart Chinese Patent Application No. 201780036168.X, dated May 28, 2020 (12 pages).
(Continued)

*Primary Examiner* — Rene T Towa
(74) *Attorney, Agent, or Firm* — Osha Bergman Watanabe & Burton LLP

(57) ABSTRACT

A method for obtaining an index for non-invasively identifying NASH is provided. A NASH determination method comprising a method for acquiring free radical consumption speed information by non-invasively detecting a redox reaction in a liver of a test animal in real time, comprises a step (1) of obtaining free radical concentration data by applying a magnetic resonance method to the liver as a measurement target after administering a probe into a body; a step (2) of
(Continued)

obtaining imaging information by processing the obtained free radical concentration data; and a step (3) of obtaining a free radical consumption speed by kinetically measuring the imaging information over time, and comprises a step of determining whether or not the test animal has NASH, based on the free radical consumption speed information obtained through application to the test animal.

8 Claims, 4 Drawing Sheets

(51) Int. Cl.
  *G01N 33/68* (2006.01)
  *G01R 33/48* (2006.01)
  *G01R 33/28* (2006.01)
  *G01N 33/50* (2006.01)
  *G01R 33/62* (2006.01)
  *A61B 5/00* (2006.01)

(52) U.S. Cl.
  CPC ............ *A61B 5/4848* (2013.01); *G01N 24/12* (2013.01); *G01N 33/50* (2013.01); *G01N 33/6893* (2013.01); *G01R 33/28* (2013.01); *G01R 33/48* (2013.01); *G01R 33/62* (2013.01); *A61B 2503/40* (2013.01); *G01N 2800/085* (2013.01)

(58) Field of Classification Search
  CPC .... G01N 24/12; G01N 33/50; G01N 33/6893; G01N 2800/085; G01R 33/28; G01R 33/48; G01R 33/62
  See application file for complete search history.

(56) References Cited

U.S. PATENT DOCUMENTS

| 2013/0056630 | A1* | 3/2013 | Feldstein | G01N 33/6893 250/282 |
| 2014/0330106 | A1* | 11/2014 | Banerjee | A61B 5/4881 600/410 |
| 2017/0003363 | A1* | 1/2017 | Rosen | G01R 33/5614 |
| 2018/0052213 | A1* | 2/2018 | Romero Gomez | G01R 33/5608 |

FOREIGN PATENT DOCUMENTS

| JP | 5837581 B2 | 12/2015 | |
| WO | WO-2011036117 A1 * | 3/2011 | ............ G01N 33/92 |
| WO | 2011/052760 A1 | 5/2011 | |

OTHER PUBLICATIONS

Office Action issued in the counterpart Japanese Patent Application No. 2018-523874, dated Jul. 21, 2020 (7 pages).
Communication pursuant to Article 94(3) issued in the counterpart European Patent Application No. 17813237.9, dated Jul. 2, 2020 (7 pages).
International Preliminary Report on Patentability for corresponding International Application No. PCT/JP2017/021524, dated Dec. 18, 2018 (5 pages).
K. Yamada et al; "Development of Integrated-type ESRI/MRI Device aiming at Non-invasive Analysis of In Vivo Redox Reaction"; The 16th Symposium on Biomedical-Analytical Science Proceedings, pp. 112-113; Aug. 2, 2003 (2 pages).
H. Tsubouchi; "Oxidation Stress and NASH"; Journal of Clinical and Experimental Medicine, vol. 206, No. 5, pp. 371-374; Aug. 2, 2013 (5 pages).
Supplemental European Search Report issued in corresponding European Patent Application No. 17813237.9, dated May 28, 2019 (8 pages).

\* cited by examiner

FREE RADICAL CONSUMPTION SPEED INFORMATION ACQUISITION METHOD AND NASH DETERMINATION METHOD

TECHNICAL FIELD

This international application is based on and claims the benefit of priority of Japanese Patent Application No. 2016-117335, filed on Jun. 13, 2016 with the Japanese Patent Office, the entire contents of which are incorporated herein by reference.

The present invention relates to a method for non-invasively acquiring free radical consumption speed information in the liver of a test animal, and a NASH determination method utilizing the method.

BACKGROUND ART

In recent years, non-alcoholic fatty liver disease (NAFLD) caused by lifestyle habits excluding drinking habits, such as dietary habits, lack of exercise and obesity, has been increasing.

NAFLD is defined as a group of diseases including liver disorders ranging from simple steatosis, to steatohepatitis, fibrosis and liver cirrhosis occurring in a person having no history of alcohol intake, but excluding viral liver disease, autoimmune liver disease and metabolic liver diseases such as hemochromatosis and Wilson disease, and is roughly divided into simple steatosis (SS) not progressing to liver cirrhosis and non-alcoholic steatohepatitis (NASH).

About 80% of NAFLD is nonprogressive and follows a benign course, but the remaining 20% progresses to NASH and evolves into liver cirrhosis and liver cancer.

With respect to how simple steatosis progresses to NASH, what is called "two hit theory" is widely known, and it is considered that fatty liver first develops as the first hit, and that liver cell damage is caused as the second hit by oxidative stress, lipid peroxidation, cytokine release caused by endotoxin and the like to progress to steatohepatitis and liver cirrhosis. It is insulin resistance that underlies these, and the selectivity in the second hit is presumed to be a genetic factor.

Therefore, it is important to differentiate NASH from NAFLD for proper treatment. However, it is known that no increase in ALT found in hematology reflects severity, and in addition, findings of fatty liver are similarly obtained by an imaging test such as abdominal ultrasound imaging or CT, and thus it is difficult to differentiate between simple steatosis (SS) following a benign course and NASH exhibiting pathological conditions progressing to hepatitis exacerbation, fibrosis, liver cirrhosis and liver cancer.

Currently, tissue diagnosis by liver biopsy is employed for definite diagnosis of non-alcoholic fatty liver disease (NAFLD)/non-alcoholic steatohepatitis (NASH) (for example, Patent Literatures 1 and 2).

However, the liver biopsy is a painful invasive test, the risk of the test itself such as inflammation is frequently pointed out, and there is the problem of low diagnostic accuracy because a tissue to be collected corresponds to merely part (a very small amount) of the whole liver and thus the collected liver tissue does not always reflect the state of the whole liver (lesion), or evaluation made for the tissue diagnosis is different among physicians responsible for the diagnosis.

From these circumstances, non-invasive diagnosis methods using a novel biomarker, an imaging test, a comprehensive scoring system and the like have been under development, but no determination method capable of definite diagnosis of NASH has been put to practical use.

On the other hand, the inventors of the present application has disclosed, in Patent Literature 3, a method for imaging an endogenous biomolecule in real time, as a method for detecting an endogenous biomolecule in a living body by utilizing a magnetic resonance method, comprising: a step of obtaining information on the endogenous biomolecule by applying a magnetic resonance method to a living body which is a subject to be measured; a step of obtaining imaging information by processing the information on the endogenous biomolecule; and a step of displaying the imaging information. However, Patent Literature 3 does not disclose a specific method for differentiating NASH.

CITATION LIST

Patent Literature

Patent Literature 1: Japanese Patent No. 5837581
Patent Literature 2: Japanese Patent No. 5252444
Patent Literature 3: International Publication No. WO2011/052760

SUMMARY OF INVENTION

Technical Problem

As described above, there is a demand for a more non-invasive and quantitative diagnosis method as a definite diagnosis method for NASH. Under these circumstances, an object of the present invention is to provide a method for obtaining an index for non-invasively identifying NASH and a NASH determination method. Besides, another object of the present invention is to provide a program to be used for the NASH determination method and a method for screening for a NASH therapeutic drug by the NASH determination method.

Solution to Problem

The present inventors have made earnest studies for solving the above-described problems and found that by detecting a redox reaction in the liver of a test animal in real time to quantitatively image free radical consumption speed information by a magnetic resonance method, and kinetically measuring the resulting information over time, a free radical consumption speed in the whole liver can be obtained, and that the obtained free radical consumption speed can be used as an index relating to development of NAFLD/NASH, leading to accomplishment of the present invention.

<1> A method for acquiring free radical consumption speed information by non-invasively detecting a redox reaction in a liver of a test animal in real time, comprising:
a step (1) of obtaining free radical concentration data by applying a magnetic resonance method to the liver as a measurement target after administering a probe into a body of the test animal;
a step (2) of obtaining imaging information by processing the obtained free radical concentration data; and
a step (3) of obtaining a free radical consumption speed by kinetically measuring the imaging information over time.
<2> The method according to <1>, wherein the free radical consumption speed information is acquired as an index for identifying non-alcoholic steatohepatitis (NASH) of the test animal.

<3> The method according to <1> or <2>, wherein the probe is a nitroxyl radical compound.

<4> The method according to any of <1> to <3>, wherein the magnetic resonance method is a DNP-MRI method.

<5> The method according to any of <1> to <4>, wherein the magnetic resonance method is applied in such a manner that a whole liver of the test animal is the target.

<6> A NASH determination method, comprising a step of determining whether or not a test animal has NASH, based on the free radical consumption speed information obtained by applying the method according to any of <1> to <5> to the test animal.

<7> The determination method according to <6>, wherein the test animal is a test animal having been diagnosed as having NAFLD.

<8> The determination method according to <6> or <7>, wherein the NASH to be determined is early-stage NASH.

<9> The determination method according to any of <6> to <8>, wherein the step of determining whether or not a test animal has NASH is a step of setting a threshold value of the free radical consumption speed based on the free radical consumption speed information in the liver of each of a known NASH-suffering animal group and a known non-NASH-suffering animal group, and determining that the test animal has NASH when the free radical consumption speed in the liver of the test animal as an evaluation target is equal to or lower than the threshold value.

<10> A NASH determination program, causing a computer to execute at least the determination method according to any of <6> to <9>.

<11> A method for screening for a NASH therapeutic drug, comprising discriminating therapeutic action of a candidate substance of a NASH therapeutic drug on NASH based on the free radical consumption speed information obtained by applying the method according to any of <1> to <5> to a test animal to which the candidate substance has been administered.

Advantageous Effects of Invention

According to the present invention, a method for obtaining an index for non-invasively identifying NASH and a NASH determination method are provided, and by non-invasively visualizing redox kinetics of the liver, the state of NASH can be evaluated, and definite diagnosis of very-early-stage NASH that cannot be detected by other diagnosis methods can be made.

Besides, according to the present invention, a program to be used for the NASH determination method and a method for screening for a NASH therapeutic drug by the NASH determination method are provided.

BRIEF DESCRIPTION OF DRAWINGS

FIG. 5A is a comparison in the free radical consumption speed between the normal mouse group and the NASH model mouse group; right.

REFERENCE SIGNS LIST

Figure 1:
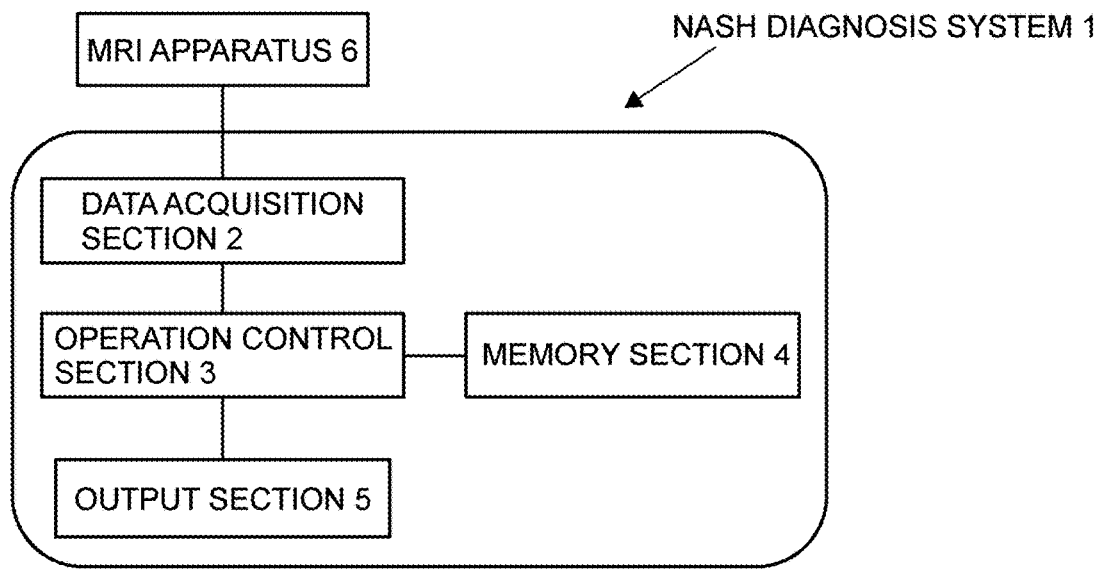
FIG. 1 is a diagram illustrating the configuration of a NASH determination system according to an embodiment of the invention.

1 NASH determination system
2 data acquisition section
3 operation control section
4 memory section
5 output section
6 MRI apparatus

DESCRIPTION OF EMBODIMENT

The present invention will be described in detail below with reference to examples and the like, and the present invention is not limited to the following examples and the like but may be practiced by being arbitrarily modified without departing from the scope of the present invention. Besides, "to" as herein used between numerical values or physical quantities is used as an expression embracing the numerical values or the physical quantities.

A first aspect of the present invention is a method for acquiring free radical consumption speed information by non-invasively detecting a redox reaction in a liver of a test animal in real time, comprising a step (1) of obtaining free radical concentration data by applying a magnetic resonance method to the liver as a measurement target; a step (2) of obtaining imaging information by processing the obtained free radical concentration data; and a step (3) of obtaining a free radical consumption speed by kinetically measuring the imaging information over time (hereinafter sometimes referred to as the "free radical consumption information acquisition method of the present invention").

According to the first aspect of the present invention, the free radical concentration data obtained by applying the magnetic resonance method to the liver through the step (1) can be visualized as the imaging information of the liver through the step (2), and the imaging information can be kinetically measured through the step (3), to obtain the free radical consumption speed in the liver. The characteristic of loss of contrast enhancement because of the disappearance of a free radical through a redox reaction caused by mitochondria in the liver is applied, and thereby the free radical consumption speed information that can be used as an index for identifying NASH can be acquired by visualization.

The test animal may be any animal to which a magnetic resonance apparatus used for evaluation can be applied to obtain a free radical consumption speed, and a human or a non-human animal can be a target. Examples of the non-human animal include, but are not particularly limited to, a mouse, a rat, a dog and a cat.

Besides, in the present invention, any substance can be a target of the imaging by the magnetic resonance method as long as the substance has a free radical, and a xenobiotic (probe) externally taken into a living body is suitably used. In particular, a probe with which a stronger signal can be obtained and which is not harmful to the test animal is preferably selected.

Examples of such a xenobiotic include a nitroxyl radical compound as a compound not harmful to a human. Examples of the nitroxyl radical compound include Carboxyl PROXYL, Tempol, Methoxycarbonyl PROXYL and Carbamoyl-PROXYL. A liver tissue is an organ metabolizing a nitroxyl radical very rapidly, and detection is difficult with a probe of Tempol, Methoxycarbonyl PROXYL or the like Besides, Carboxyl PROXYL does not have cell membrane permeability and thus is effective for redox analysis in a blood vessel but analysis in a liver cell is difficult. Carbamoyl-PEROXYL is suitably used because it is low toxic, has cell membrane permeability and is metabolized slowly.

Therefore, usually after administering a probe into a body of the test animal, the magnetic resonance method is applied to the liver as the measurement target. In other words, the magnetic resonance method is usually applied to the liver of the test animal into the body of which the probe has been administered, to obtain the free radical concentration data.

The magnetic resonance method used in the present invention is a general magnetic resonance method, wherein a phenomenon that when electromagnetic waves or an oscillating magnetic field is externally applied to a measurement target, a kind of resonance is caused at a specific frequency to strongly absorb electromagnetic waves (magnetic resonance) is utilized to measure the state of an electron or an atomic nucleus inside a substance based on the frequency at which resonance absorption occurs or the waveform of the absorption.

Examples of the magnetic resonance method include a magnetic resonance imaging (MRI) method, a DNP-MRI method, a nuclear magnetic resonance (NMR) method and an electron spin resonance (EPR) method. In particular, the DNP-MRI method using a dynamic nuclear polarization (DNP)-MRI apparatus and the electron spin resonance method are suitable, and a more accurate measurement image can be obtained by employing these magnetic resonance methods. When the DNP-MRI method having particularly high sensitivity is used, a free radical concentration can be quantitatively imaged, and thus the free radical consumption speed information that can be used as the index for identifying NASH can be more accurately acquired.

In the present invention, the magnetic resonance method is preferably applied to target not only part of the liver but also the whole liver. Thereby, the free radical consumption speed information in the whole liver can be discriminated. As a result, the redox kinetics of the whole liver can be quantitatively visualized.

A second aspect of the present invention is a NASH determination method comprising a step of determining whether or not a test animal has NASH, based on the free radical consumption speed information obtained by applying the method of the first aspect of the present invention to the test animal (hereinafter referred to as the "NASH determination method of the present invention"). As described above, in the free radical consumption information acquisition method of the first aspect of the present invention, the free radical concentration data obtained by applying the magnetic resonance method to the liver can be visualized as imaging information of the liver, the imaging information can be kinetically measured over time, to non-invasively obtain the free radical consumption speed in the liver of the test animal in real time, and based on this free radical consumption speed information, it is determined whether or not the test animal has NASH.

According to the NASH determination method of the present invention, determination can be made on early-stage NASH, which was difficult to identify by a conventional non-invasive method. By applying the NASH determination method of the present invention to a test animal that has been diagnosed as having NAFLD by another known method, the definite diagnosis of early-stage NASH can be effectively made.

As used herein, the term "early-stage NASH" refers to NASH at stage 1 or 2 according to the Brunt staging system, and the term "progressive NASH" refers to NASH at stage 3 or 4 according to the Brunt staging system.

In a preferable aspect of the NASH determination method of the present invention, the step of determining whether or not a test animal has NASH is a step of setting a threshold value of the free radical consumption speed based on the free radical consumption speed information in the liver of each of a known NASH-suffering animal group and a known non-NASH-suffering animal group, and determining that the test animal has NASH when the free radical consumption speed in the liver of the test animal as an evaluation target is equal to or lower than the threshold value.

A third aspect of the present invention is a NASH determination program for causing a computer to execute the NASH determination method of the present invention (hereinafter referred to as the "program of the present invention"). In the program of the present invention, not only the NASH determination method of the present invention but also data for execution of another method may be incorporated.

Besides, the NASH determination method of the present invention (the second aspect of the present invention) may be applied to screen for a NASH therapeutic drug.

Specifically, a fourth aspect of the present invention is a method for screening for a NASH therapeutic drug, comprising discriminating therapeutic action of a candidate substance of a NASH therapeutic drug on NASH based on the free radical consumption speed information obtained by applying the free radical consumption information acquisition method of the present invention to a test animal to which the candidate substance has been administered. As described above, even early-stage NASH can be discriminated by the NASH determination method of the present invention, and thus a beneficial NASH therapeutic drug can be more efficiently screened for.

As an exemplified embodiment of the present invention, a NASH determination system used for performing the NASH determination method of the present invention will be described below with reference to the drawings. It is noted that the embodiment described below is illustrative in all respects and is not limiting. In particular, items not clearly disclosed in the embodiment disclosed herein, such as operating conditions and process conditions, various parameters, and the dimensions, the weight and the volume of each element, do not depart from those usually employed by those skilled in the art, and values that can be easily assumed by those skilled in the art are employed.

FIG. 1 illustrates the configuration of a NASH determination system 1 according to the embodiment of the present invention. The NASH determination system 1 functionally is composed of a computer including a data acquisition section 2, an operation control section 3, a memory section 4 and an output section 5, and an MRI apparatus 6.

The data acquisition section 2 is connected to the MRI apparatus 6, has the function of acquiring data of the magnetic resonance method, and acquires MRI data obtained by the MRI apparatus 6. The connection between the data acquisition section 2 and the MRI apparatus 6 may be wired or wireless. Besides, a configuration in which MRI data acquired in an external agency such as another hospital is received through a network may be employed.

The operation control section 3 has the functions of executing the NASH determination program stored in the memory section 4 and determining whether or not a test animal as a test target has NASH by using the MRI data acquired by the data acquisition section 2.

The memory section 4 stores a program for activating the NASH determination system 1 and the NASH determination program. Besides, the memory section 4 stores the threshold value (cut-off value) for determining NASH. The threshold value in the memory section 4 is determined according to the type, the age, the sex and the like of the test animal.

The output section 5 outputs a NASH determination result from the operation control section 3 to the outside. An output method is usually display on a monitor included in the NASH determination system 1, or a configuration in which the result is transmitted to the outside through a network may be employed.

The MRI apparatus 6 is a DNP-MRI apparatus capable of executing a DNP-MRI method (Overhauser MRI method). As such an apparatus for imaging by the magnetic resonance method, for example, an apparatus disclosed in International Publication No. WO2010/110384, namely, "an apparatus comprising a magnetic field generator for generating a magnetic field to excite magnetic resonance of an object to be measured, a mover for moving one of the object to be measured and the magnetic field generator to thereby move the object to be measured in the magnetic field generated by the magnetic field generator, a measurement unit for applying a gradient magnetic field in at least one of a moving direction "y" in which the object to be measured moves relative to the magnetic field generator, and a direction "x" perpendicular to the moving direction "y" to thereby obtain image signals of the object to be measured by virtue of at least one of phase-encoding and frequency-encoding without stopping the object to be measured or the magnetic field generator while they are being moved by the mover, and a correction unit for eliminating influence on the image signals derived from movement of the object to be measured in the moving direction "y" to provide corrected image signals," can be used.

An example (Example) in which a system having a similar configuration to that of the NASH determination system 1 of the present embodiment was used and a NASH model mouse was used as a test animal to acquire free radical consumption speed information for determining whether or not the test animal had NASH (an Example) will be described below. It is noted that the present invention is not limited to the Example.

EXAMPLE (Test Animal)

The NASH model mouse was prepared as follows. All the procedures and handling of animals were approved by the Animal Care and Use Committee at the Faculty of Pharmaceutical Sciences of Kyushu University, and the experiment was carried out according to the Institutional Guidelines for Animal Experiments at the Faculty of Pharmaceutical Sciences of Kyushu University.

C57BL6 mice (female, 5 weeks old) were purchased from Charles River Laboratories Japan, Inc. (Yokohama, Japan), and were acclimated for 1 week before starting the experiment. Five mice were housed per cage and were fed with a methionine-choline deficient diet or a normal diet in a room where the temperature and the circadian rhythm were controlled. Each of a methionine-choline deficient diet group (NASH model mouse group) and a normal diet group (normal mouse group) was divided into 5 groups to be subjected to DNP-MRI measurement at 1, 2, 4, 6 and 8 weeks, and blood collection, autopsy and liver tissue collection were performed to evaluate the pathological conditions.

(DNP-MRI Evaluation)

Figure 2:
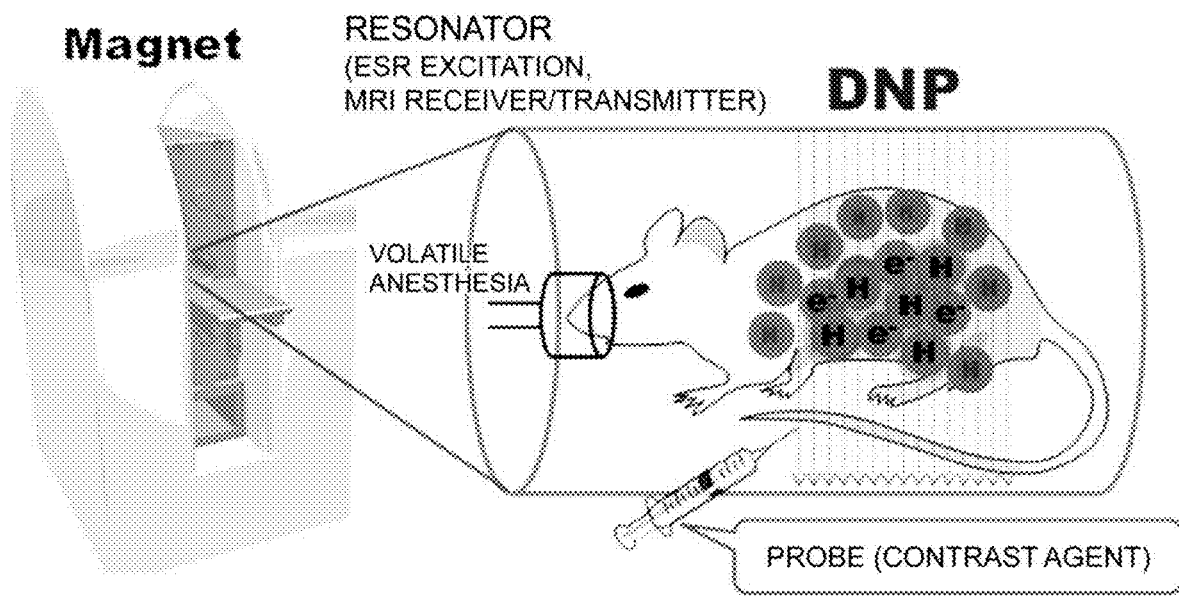
FIG. 2 is a schematic diagram illustrating how DNP-MRI evaluation is made.

FIG. 2 is a schematic diagram illustrating how DNP-MRI evaluation is made.

A mouse (NASH model mouse) was anesthetized with isoflurane (4% for introduction, 2% for maintenance) and was fixed, with a pressure-sensitive tape for skin, on a local detector for liver measurement (a surface coil) and a holder with the stomach side faced downward. The body temperature of the mouse was 37±1° C. during the experiment. The mouse was transferred to a DNP-MRI resonance apparatus and the apparatus was set such that the whole liver was a measurement target, and then, CmP (Carbamoyl-PROXYL, redox contrast agent) was intravenously injected into the NASH mode mouse, and the DRI-MRI measurement was started.

The conditions for the DRI-MRI are as follows:

TR: 1200 ms; TE: 25 ms; TEPR: 600 ms; number of phase-encoding gradient steps: 64; NEX: 4; FOV: 48 mm×48 mm; matrix size: 64×64 (in-plane resolution: 0.75 mm); slice thickness: 30 mm; number of average: 1; and scanning time: 79 s. OMRI data was analyzed by using Image J Software Package (http://rsb.info.nih.gov/ij/).

Besides, the mouse group fed with the normal diet (the normal mouse group) was similarly subjected as a control to the DRI-MRI evaluation.

(Results)

Figure 3:
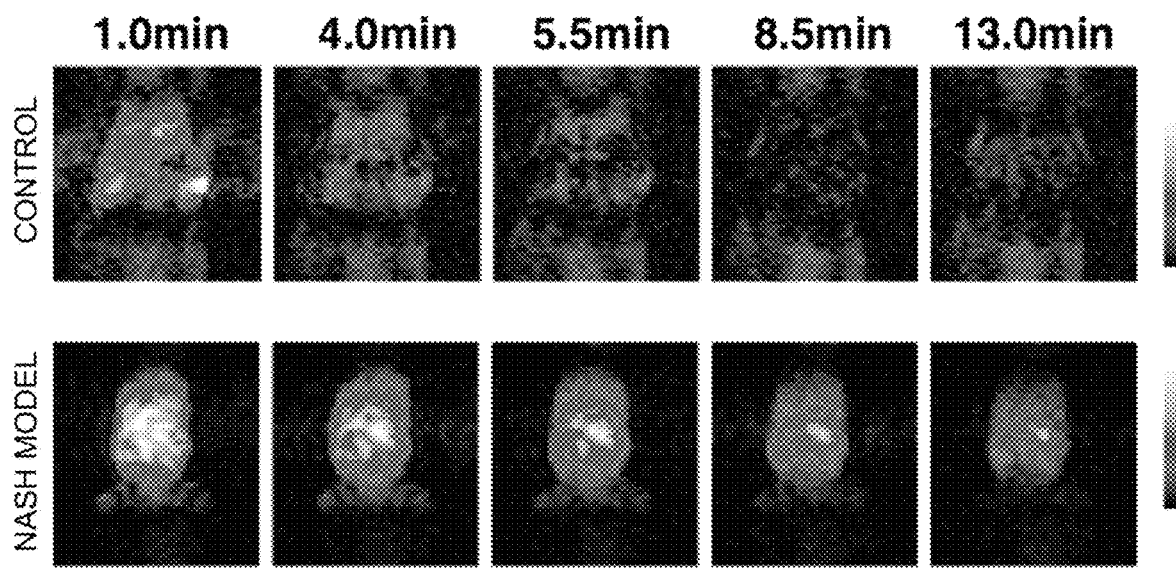
FIG. 3 illustrates DNP-MRI images (in vivo imaging) obtained over time by DNP-MRI of the epigastrium of mice to each of which a redox contrast agent (CmP) has been administered by intravenous injection (upper: normal mice (control mice); lower: NASH model mice).

FIG. 3 illustrates DNP-MRI images (in vivo imaging) obtained over time by the DNP-MRI of the epigastrium of mice to each of which the redox contrast agent (CmP) had been administered by intravenous injection (upper: normal mice (control mice); lower: NASH model mice).

In the normal mice (control), it is understood that the CmP was homogeneously distributed in the epigastrium, then rapidly disappeared over time because of redox metabolism of the CmP radical, and mostly disappeared 5.5 minutes and more after the administration of the CmP. On the other hand, in the NASH model mouse (NASH model), it is understood that a signal with high intensity derived from the CmP present in the epigastrium was observed after the administration of the CmP, and that the redox metabolism gradually proceeded thereafter. As described above, the reduction rate of the CmP radical was obviously lower in the NASH model mouse than in the normal mouse, and the CmP radical remained even 13 minutes after the administration of the CmP.

When a region with image intensity of each of the NASH model mouse and the normal mouse was selected as a region of interest, and changes in the intensity were plotted, it was found that the disappearance of the CmP in the NASH model mouse was significantly slower than in the normal mouse. This result revealed that information on the CmP radical consumption speed in a mouse liver can be obtained by the free radical consumption information acquisition method of the present invention.

Figure 4:
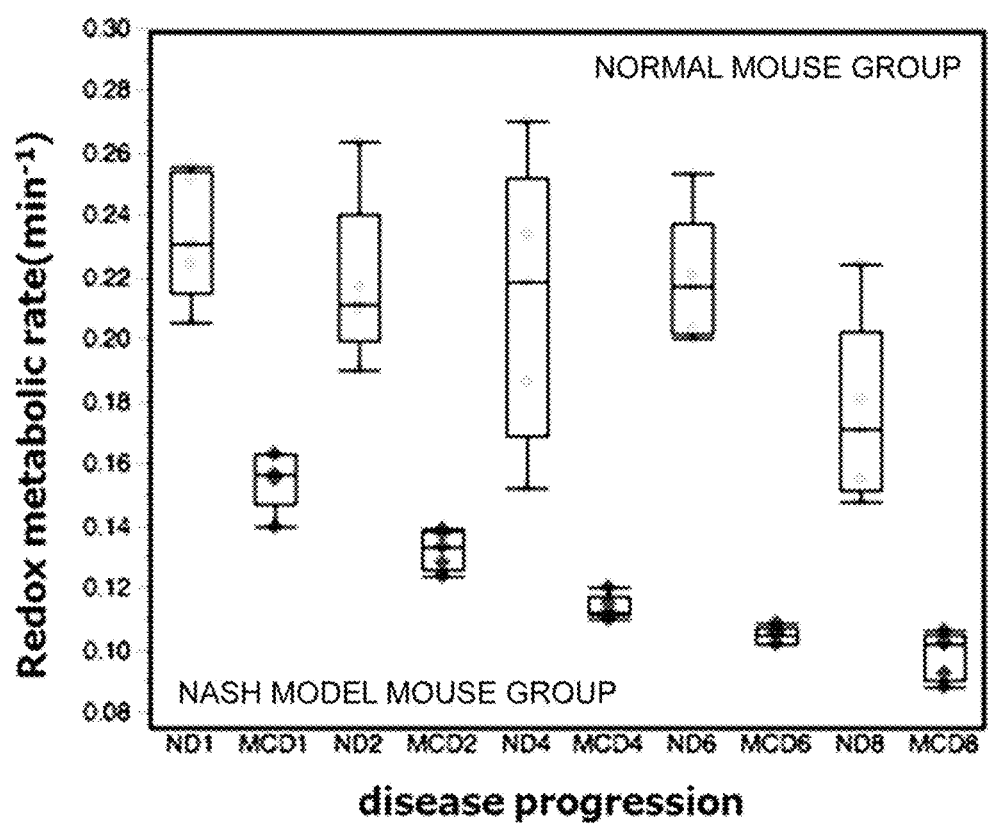
FIG. 4 is a diagram illustrating a free radical consumption speed and disease progression in a normal mouse group (control mouse group) and a NASH model mouse group, which is obtained by plotting values of redox metabolic rates in the liver calculated by extracting a liver part from the images of FIG. 3 as a region of interest (ROI).

Besides, FIG. 4 is a diagram illustrating redox metabolic rate (free radical consumption speed) and disease progression in the normal mouse group (control mouse group) and the NASH model mouse group, which is a diagram obtained by plotting values of redox metabolic rates in the liver calculated by extracting a liver part from the images of FIG. 3 as a region of interest (ROI).

With respect to the NASH model mouse group, the DNP-MRI measurement was performed 1 week (MCD1), 2 weeks (MCD2), 4 weeks (MCD4), 6 weeks (MCD6) and 8 weeks (MCD8) after feeding the methionine-choline deficient diet (MCD) was started, and the redox metabolic rate of the CmP radical in the liver was calculated. When the redox metabolic rate significantly decreases, it is determined that the mouse has the pathological condition of NASH.

Also with respect to the normal mouse group, the DNP-MRI measurement was similarly performed 1 week (ND1), 2 weeks (ND2), 4 weeks (ND4), 6 weeks (ND6) and 8 weeks (ND8) after feeding the normal diet was started, and the redox metabolic rate of the CmP radical in the liver was calculated.

As illustrated in FIG. 4, the redox metabolic rate of the CmP in the liver was 0.17 to 0.23 $min^{-1}$ in the normal mouse, indicating a comparatively rapid redox metabolic rate mainly due to redox metabolism in the mitochondrial electron transport chain.

On the other hand, in the NASH model mouse group, significant decrease in the redox metabolic rate (disappearing rate) is found even in 1 week (MCD1), and the redox metabolic rate decreases over time.

In FIG. 4, the threshold value for determining NASH is set to 0.16 $min^{-1}$, and when the redox metabolic rate of a test mouse was lower than this threshold value, the mouse was considered to have NASH.

Also in the case of a human, NASH in a human can be similarly diagnosed by using the redox metabolic rate. Specifically, it is assumed that the redox metabolic rate is in a certain range of metabolic rate in a human with a healthy liver or simple fatty liver. On the other hand, the redox metabolic rate significantly decreases at an early stage in the liver of a NASH patient, and thus if a threshold value of the redox metabolic rate in a healthy human or a human with a fatty liver is determined, the human can be diagnosed as having NASH if the redox metabolic rate is lower than the threshold value.

Figure 5A:
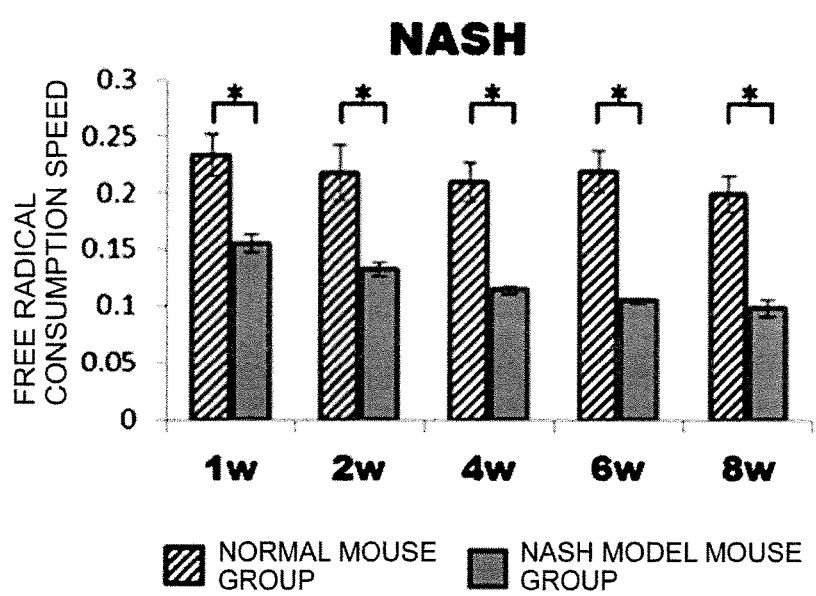
FIG. 5A illustrates measurement results of the redox metabolic rate over time in the liver obtained by in vivo DNP-MRI according to the present invention (left.
Figure 5B:
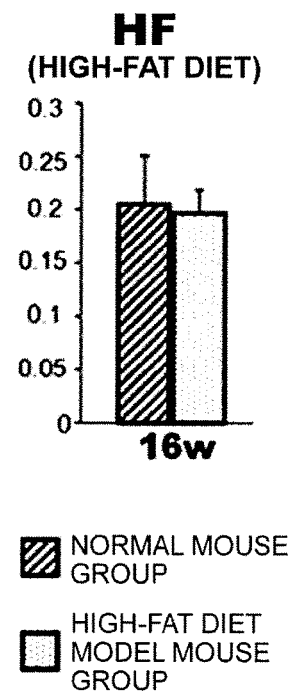
FIG. 5B is a comparison in the free radical consumption speed between the normal mouse group and a high-fat diet (HF) model mouse group).

Besides, FIGS. 5A-5B illustrate measurement results of the redox metabolic rate (free radical consumption speed) over time in the liver obtained by in vivo DNP-MRI according to the present invention. FIGS. 5A-5B illustrate averages of calculated values of the redox metabolic rate in the liver of the normal mouse group and the NASH model mouse group obtained by a method similar to that of FIG. 4, and also illustrates a result obtained in a fatty liver mouse group fed with a high-fat diet. FIG. 5A (left) illustrates results obtained in the normal mouse group and the NASH model mouse group, and FIG. 5B (right) illustrates results obtained in the normal mouse group and the high-fat diet (HF) fatty liver mouse group. In an experiment using a high-fat diet (HF) model mouse for inducing a state of fatty liver alone in a mouse, there was no significant difference in the free radical metabolism in the liver from the normal mouse group. These results show that the state of fatty liver (NAFLD) cannot be determined as NASH by the NASH determination method of the present invention but a pathological condition of NASH can be detected based on the redox metabolic reaction only when liver exhibits the pathological condition of NASH. In other words, it is shown that NAFLD and NASH can be distinguishably determined.

Also in the case of a human, similarly by employing the NASH determination method of the present invention for a human with simple fatty liver (NAFLD) and a NASH patient, the both can be precisely distinguishably diagnosed.

Figure 6:
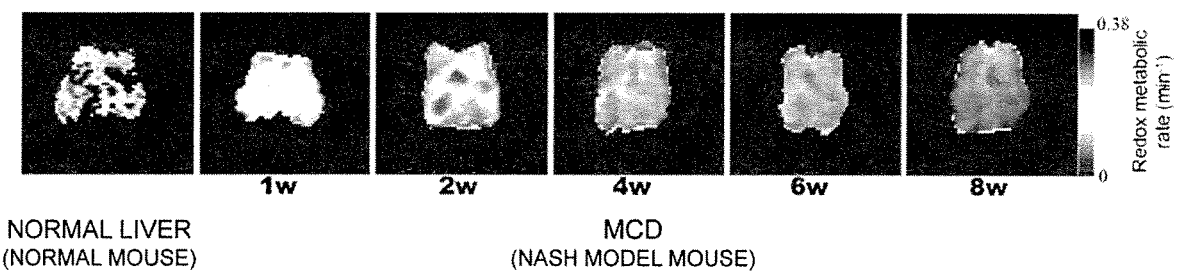
FIG. 6 illustrates images of variation in early-stage lesions of NASH obtained by the in vivo DNP-MRI according to the present invention.

FIG. 6 is an explanatory diagram of imaging of variation in early-stage lesions of NASH obtained by the in vivo DNP-MRI according to the present invention. As illustrated in FIG. 6, an image of the redox metabolism is effective for visually diagnosing NASH. It is noted that although FIG. 6 illustrates gray images, color images are used in actual diagnosis, and the color of the liver that is normal and the color of a lesion of NASH are distinguished from each other based on the free radical consumption speed in the liver. Thereby, if the color (of, for example, blue) of the liver that is normal is changed and shifted from a specific color to another specific color (for example, from yellow to red), NASH can be easily visually diagnosed.

Figure 7:
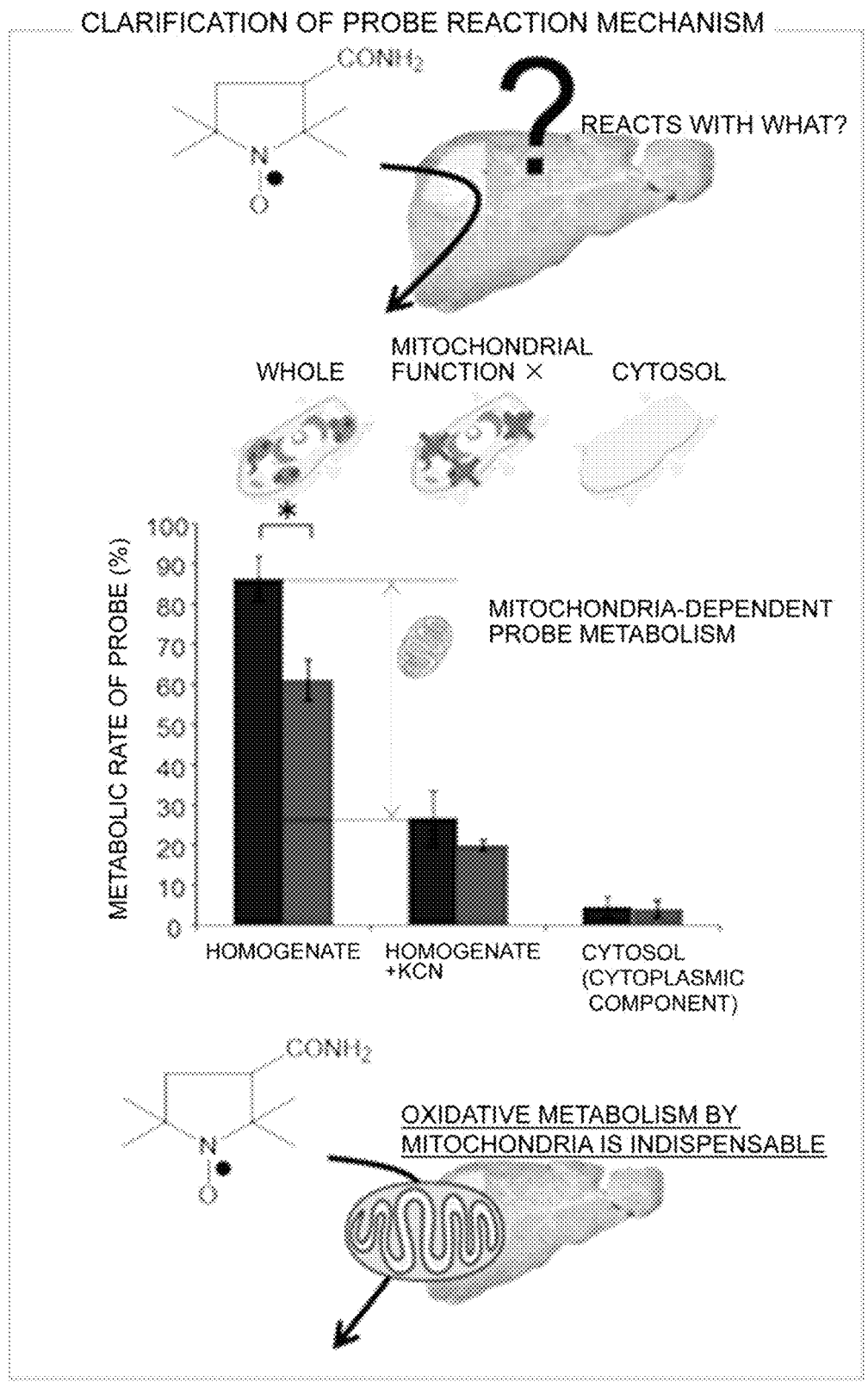
FIG. 7 is an explanatory diagram of a reaction mechanism of the redox contrast agent (CmP) according to the present invention.

Besides, FIG. 7 is an explanatory diagram of a reaction mechanism of the CmP (redox contrast agent) according to the present invention. It has been revealed through experiments that the CmP, which is the redox contrast agent (probe) used herein, minimally reacts with a cytoplasmic component or a blood component. As illustrated in FIG. 7, the CmP is redox metabolized by a homogenate solution of the liver, but the metabolism is stopped when KCN, which is a mitochondrial electron transport chain inhibitor, is added, indicating that the CmP uses, as an index, the redox metabolism through the mitochondrial electron transport chain.

INDUSTRIAL APPLICABILITY

The present invention is useful because definite diagnosis of NASH can be non-invasively made for a test animal.

The invention claimed is:

1. A method for non-invasively determining the presence of a non-alcoholic steatohepatitis (NASH) in a test animal, comprising:
    determining a first redox metabolic rate in livers of a known NASH-suffering animal group;
    determining a second redox metabolic rate in livers of a known non-NASH-suffering animal group;
    setting a threshold value based on the first and second redox metabolic rates; and
    determining that the test animal has NASH when a determined redox metabolic rate in a liver of the test animal is equal to or lower than the threshold value,
    wherein the redox metabolic rate represents a redox metabolism via the mitochondrial electron transport chain in the liver of the test animal and is determined by:
        obtaining free radical concentration data by applying a magnetic resonance method to at least a portion of the liver as a measurement target after administering a probe into a body of the test animal;
        obtaining imaging information by processing the obtained free radical concentration data; and
        kinetically measuring the imaging information over time.

2. The method according to claim 1, wherein the probe is a nitroxyl radical compound.

3. The method according to claim 1, wherein the magnetic resonance method is a dynamic nuclear polarization magnetic resonance imaging (DNP-MRI) method.

4. The method according to claim 1, wherein the magnetic resonance method is applied to the whole liver.

5. The method according to claim 1, wherein the test animal is diagnosed as having non-alcoholic fatty liver disease (NAFLD).

6. The method according to claim 1, wherein NASH includes an early-stage NASH in the test animal.

7. The method according to claim 1, further comprising causing a computer to execute using the determined redox metabolic rate to determine the presence of NASH in the test animal.

8. A method of screening for a therapeutic drug for non-alcoholic steatohepatitis (NASH), comprising:
  administering a candidate substance of a therapeutic drug for NASH into a body of a test animal;
  obtaining free radical concentration data by applying a magnetic resonance method to at least a portion of a liver of the test animal as a measurement target after administering a probe into a body of the test animal;
  obtaining imaging information by processing the obtained free radical concentration data;
  determining a redox metabolic rate by kinetically measuring the imaging information over time; and
  discriminating therapeutic action of the candidate substance of a therapeutic drug for NASH based on the redox metabolic rate.

* * * * *